United States Patent [19]

Karmann et al.

[11] 4,299,231

[45] Nov. 10, 1981

[54] ELECTRICALLY CONDUCTIVE, VISCO-ELASTIC GEL AND ITS USE IN ELECTRODE

[75] Inventors: Werner Karmann; Gerd Weidehaas; Bernd Höwe; Frank Piel, all of Hamburg, Fed. Rep. of Germany

[73] Assignee: Beiersdorf Aktiengesellschaft, Hamburg, Fed. Rep. of Germany

[21] Appl. No.: 93,256

[22] Filed: Nov. 13, 1979

Related U.S. Application Data

[63] Continuation-in-part of Ser. No. 912,638, Jun. 5, 1978, abandoned.

[30] Foreign Application Priority Data

Jun. 18, 1977 [DE] Fed. Rep. of Germany ....... 2727396

[51] Int. Cl.$^3$ .......................... H01B 5/16; H01B 1/20; H01B 17/64; A61B 5/04
[52] U.S. Cl. .................................... 128/639; 106/208; 128/803; 252/316; 252/500; 252/518
[58] Field of Search ...................... 252/316, 518, 500; 128/803, 639, 640; 106/208

[56] References Cited

U.S. PATENT DOCUMENTS

| | | | |
|---|---|---|---|
| 2,439,460 | 4/1948 | Engler | 106/208 |
| 2,555,037 | 5/1951 | Jensen | 252/518 X |
| 3,048,549 | 8/1962 | Adams | 252/518 |
| 3,567,657 | 3/1971 | Lichtenstein | 252/521 X |
| 3,658,726 | 4/1972 | Mühl | 252/316 X |
| 3,665,064 | 5/1972 | Mosier et al. | 252/514 X |

*Primary Examiner*—Richard D. Lovering
*Attorney, Agent, or Firm*—Bierman & Bierman

[57] ABSTRACT

A visco-elastic gel comprising a high molecular weight polysaccharide, at least one polyol and, optionally, at least one non-volatile acid soluble in the polyol and at least one non-volatile base soluble in the polyol. The polyol has a water content of 5 to 20 percent by weight and the various components set forth are physiologically acceptable. The gel is particularly suitable as a means for releasably securing an electrode to the skin as, for example, when taking an EEG or EKG. Methods of making a suitable electrode and using it are also disclosed.

3 Claims, No Drawings

ELECTRICALLY CONDUCTIVE, VISCO-ELASTIC GEL AND ITS USE IN ELECTRODE

This application is a continuation-in-part of application Ser. No. 912,638, filed June 5, 1978 and now abandoned which, in turn, claims the priority of German Application No. P 27 27 396.7 filed June 18, 1977.

The present invention is directed to electrically conductive, visco-elastic gels, particularly those which are suitable for use in electrodes for medical purposes.

In the course of medical treatment and/or diagnosis, it is sometimes desirable to connect an electrical instrument to the skin of the patient in order to measure certain responses in the human body. For example, some forms of electrotherapy require such connections, as do EKG and EEG tests. A particularly critical point is the passage of current between the surface of the skin and the electrical contact connected by wire to the device. Such a connection should have a low stable resistance which does not vary with time, humidity, etc.

It has been found increasingly desirable to use self-adhesive electrodes as suitable contact elements for such instruments. These are generally discarded after a maximum of a very few uses. Such elements generally comprise a conductor which is connected to the line wires, a means for making contact with the surface of the skin, and a self-adhesive flexible flat material (such as a plaster strip) by means of which the contact is firmly fixed to the skin.

Such prior art electrodes are generally affixed to the skin by a soft, pasty or gel-like electrolyte having a high water content. This material is either applied directly to the skin immediately prior to each measurement, or is retained firmly in ready-to-use electrodes by an absorbent cushion; e.g. an open-pored foam, or else the electrolyte is held in a chamber associated with the electrode.

Such materials have two substantial drawbacks. First of all, their conductivity and fluidity are determined primarily by the amount of water contained therein. If they are stored in the open in an ordinary room having a 30 to 50 percent relative humidity, a large portion of the water evaporates so that the conductivity is reduced to such an extent that the electrode can become useless. Such deterioration in electrical characteristics cannot be completely prevented even by careful and costly sealing and packing of the electrodes. Secondly, after the contact elements are removed from the skin, an undesirable residue of the electrolyte remains. This is frequently difficult to remove.

It is, therefore, an object of the present invention to provide a contact element which overcomes the aforementioned drawbacks. Such contacts insure trouble-free passage of the electric current, even after prolonged storage, and leave no residues on the skin. In addition, the present invention is easy and cheap to manufacture and, for that reason, is readily produced in disposable form.

The present invention comprises an electrically conductive, visco-elastic gel which is used to cement the contact to the skin. The gel comprises as components 10 to 50 percent of a high molecular weight polysaccharide, 90 to 20 percent of at least one polyol, 0 to 30 percent of at least one non-volatile acid soluble in said polyol, and 0 to 30% of at least one non-volatile base soluble in said polyol. The percentages are by weight based on the total amount of the gel. In addition, the polyol has a water content of 5 to 50 percent by weight of said polyol.

Of course, all of the ingredients are physiologically acceptable to the skin. Such substances are well known to the person of ordinary skill in the art, and he will have no difficulty in selecting appropriate ones from the classes of material set forth. In addition, small amounts of the usual additives or assistants may be added as is known in the art.

The term "visco-elastic" as used herein means that the gel exhibits both viscous and elastic behavior. This characteristic is also known as "reversible compliance" and is measured by pressing on the surface of the gel and observing the depth to which it depresses and the amount of "spring back" after the pressure is removed. The elastic behavior is further determined by stretching the gel until it ruptures. The gels of the present invention have sufficient flowability so that they wet the small irregularities of the skin and, at the same time, have sufficient cohesiveness so that they can be peeled off the skin without leaving any residue.

These gels, in which the polyol acts as both a swelling agent and a plasticizer for the polysaccharide, possess excellent conductivity. It is believed that this characteristic stems from the protons of the carboxyl group of the poly (hetero) saccharides and/or of the acid, in the event that it has been included.

The acids used are preferably polybasic, preferably citric or phosphoric acids. The polyols preferably contain 10 to 20 percent of water by weight. Most preferred are such polyols as ethylene glycol, propylene glycol, glycerine and homologous $C_4$ alcohols.

In a particularly advantageous form of the invention, the acid present can be neutralized by a base to obtain the most desirable pH of 4 to 5, which is extremely good for use on the skin.

The preferred concentration range of polysaccharide is from 10 to 40 percent by weight based on the total gel. The corresponding preferred range of polyols is 90 to 60 percent by weight. The preferred amounts of acid and base are 5 to 30 percent by weight of each.

In order to obtain the desired visco-elastic properties of the gel, the polysaccharide should have a high molecular weight. In most cases, a mean molecular weight of at least about $10^6$ is required. If this limitation is not met, the gel will usually not have the necessary cohesiveness so that it can be removed from the skin without leaving any residue.

The most desired polysaccharides are water soluble ones, such as gum karaya, gum tragacanth, xanthan gum, and carboxymethylcellulose. It has been found that the gum karaya yields the best results, probably because of its high molecular weight of about $9.5 \times 10^6$ (see Ullmann, Volume 13, pages 167 et seq.).

Of course, the usual additives to such compositions may be incorporated without impairing the unique properties of the gels according to the present invention. Such things as preservatives, stabilizers, dyes, etc. are incorporated into these compositions without difficulty. Such additives should, of course, be compatible with the other ingredients and physiologically acceptable.

For best results, the polyols used should have a gelling capacity for the polysaccharide which produces the solid visco-elastic body only after a time delay. This provides an opportunity to shape the body before it sets. As previously mentioned, ethylene glycol, propylene glycol, glycerine and homologous $C_4$ alcohols are suitable for this purpose. Glycerine has been found to be most desirable of the polyols listed.

The acids and bases which are optionally added to the gel, can be used to adapt them to specific requirements. Such materials can be inorganic or organic, so long as they are soluble in the polyol and are physiologically acceptable. In particular, a mixture of equal parts of citric acid and triethanolamine has been found desirable. Such a mixture produces a pH of about 4.3.

While the gel of the present invention can be used to affix various types of electrodes because of its good conductivity, it is particularly suitable for medical purposes. It grips the skin tightly, insures a trouble-free passage of current, and can be removed easily without leaving any residue on the skin. In addition, it is hydrophilic. This enables it to absorb the moisture which is usually secreted by the skin without losing its adhesiveness or other valuable properties, including its electrical conductivity.

Since these gels have a relatively low water content, they can be stored open to the air. If this is done, they will not dry out as do the conventional high water content pastes and gels of the prior art. The latter become unusable as their electrical resistance increases. These characteristics, coupled with the self-adhesiveness of the compositions, make it possible to produce simple and cheap electrodes from them. They require neither special devices for receiving the conductor gel, nor expensive and difficult sealing and packing.

In its simplest form, an electrode according to the present invention can be made of a small, flexible piece of a carrier strip provided with a self-adhesive composition. For example, a woven or nonwoven fabric having a conductor of metal (or any other material that has been rendered conductive) passing through its center. The conductor is surrounded at one end (the side to be applied to the skin) by a small disc of the gel of the present invention. It is connected at its other end by means of the usual wires to the appropriate electrical device.

In order to facilitate handling, the adhesive side of the electrode is covered with an easily removable sheet material to protect it until it is ready to be used. Similarly, the opening on the nonadhesive side of the carrier can be surrounded by a foil ring (or the like), particularly when the carrier is very thin. These electrodes can be produced and packed individually, or in the form of a continuous tape from which they are cut off as needed.

The following examples are intended to illustrate the invention.

EXAMPLES 1 to 14

These examples indicate the production of conductive gels of the present invention by the use of the high molecular polysaccharide material known as gum karaya. This gum comprises the dried exudate of the tree Sterculia urens, found in India. It is an acetylated polysaccharide having a molecular weight of about $9.5 \times 10^6$.

The components 2 through 6 as set forth in Table 1 are dissolved at about 80 degrees C. Thereafter, the mixture is cooled to 10 degrees C., and the karaya powder was slowly stirred in. The mass was poured into molds of 15 mm diameter and 2 mm thickness, gelled for three minutes at 80 degrees C., and removed from the mold after cooling to room temperature.

TABLE 1

| Example | (in % by weight) | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| 1. Karaya-powder | 10 | 15 | 20 | 25 | 30 | 20 | 20 | 20 | 20 | 20 | 20 | 40 | 20 | 20 |
| 2. glycerin (15% water) | 70 | 65 | 60 | 55 | 50 | 50 | 67 | 40 | 80 | 70 | 45 | 40 | 58 | 58 (1) |
| 3. citric acid | 10 | 10 | 10 | 10 | 10 | — | 10 | 20 | — | 5 | 10 | 10 | 10 | 10 |
| 4. phosphoric acid | — | — | — | — | — | 20 | — | — | — | — | — | — | — | — |
| 5. triethanol amine | 10 | 10 | 10 | 10 | 10 | 10 | — | 20 | — | 5 | 25 | 10 | — | — |
| 6. NaOH (50%) | — | — | — | — | — | — | 3 | — | — | — | — | — | 12 | 12 |
| pH-value (2) | 4.3 | 4.3 | 4.2 | 4.1 | 4.2 | 1.7 | 3.0 | 4.2 | 4.5 | 4.2 | 7.7 | 4.2 | 6.2 | 6.2 |

(1) 90% glycerin for compensating the water content of the NaOH solution
(2) Measurement of the pH-value with an Ingold skin electrode after wetting the surface with a little water

COMPARISON EXAMPLES A AND B

From two conductive gels, contact elements were produced wherein the substances were adsorbed onto polyurethane foam. Example A comprises a conductive gel from a commercial self-adhesive electrode ("Red Dot" produced and sold by Minnesota Mining and Manufacturing Co.). Example B was a conductive gel in accordance with German Pat. No. 2,302,618 (Example 2). It comprises the following composition:

| 79.1 | parts by weight | water |
|---|---|---|
| 2.4 | " | Carbopol 940 |
| 3.0 | " | triethanolamine |
| 0.5 | " | 2-chloro-m-xylenol |
| 15.0 | " | sodium sulfate (anhydrous) |

In order to compare the present invention (Examples 1 to 14) with the prior art (Examples A and B), simple electrodes were made from a round piece of non-woven carrier material coated on one side with a self-adhesive composition. A small conductor of a polyester web (made conductive with graphite) passes through the center of the material and a small flat gel disk was applied to the skin side of the conductor. Each of the gels of Examples 1 to 14 and Examples A and B were used.

These electrodes were stored for 17 hours at 21°–23° C. and a relative humidity of 55–65%. The weight loss or gain was measured at the end of that period.

In addition, 2 such electrodes were pasted on the underarm 30 cm apart and the resistance between the two was determined by the use of a Digimeter 704 manufactured by HEB. This device measured in the range of 20 megaohms. The results are set forth in Table 2.

TABLE 2

| Example | Weight Difference (%) | Skin Resistance (Megaohm) Fresh | After Storage for 17 h |
|---|---|---|---|
| 1 | +3.5 | 0.41 | 0.57 |
| 2 | +2.0 | 0.65 | 0.78 |
| 3 | +1.5 | 0.27 | 0.40 |
| 4 | +1.3 | 0.20 | 0.35 |
| 5 | +0.5 | 0.40 | 0.65 |
| 6 | +2.0 | 0.21 | 1.20 |
| 7 | +0.1 | 0.49 | 0.92 |
| 8 | +1.6 | 0.51 | 0.72 |
| 9 | +1.9 | 0.07 | 0.48 |
| 10 | +1.8 | 0.39 | 0.43 |
| 11 | +3.5 | 0.19 | 0.74 |
| 12 | −0.4 | 0.70 | 1.10 |
| 13 | −2.7 | 0.16 | 0.23 |
| 14 | −0.7 | 0.15 | 0.32 |
| A | −77 | 0.23 | infinite |
| B | −63 | 0.07 | infinite |

It will be appreciated that, since there are no other volatile components contained in the various mixtures, the loss or gain of weight is a direct measure of the loss or absorption of water from the atmosphere.

As can be seen from the foregoing results, the gels of the present invention exhibit virtually no weight change, even after open storage for 17 hours. In addition, there is very little increase in their advantageously low skin resistance. The prior art gels, which had a high water content, show a total loss of their conductivity so that they are rendered completely useless.

In addition to the foregoing, further tests of the present invention indicate that, after being affixed to the skin for 3 hours, the electrodes can easily be removed, leaving no residue. The prior art substances, on the other hand, left a smudgy film when they were removed.

EXAMPLES 15 to 29

Various additional conductive gels according to the present invention were produced as set forth in Table 3.

They all demonstrated the same advantageous characteristics of the gels of Examples 1 to 14.

TABLE 3

| Example | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|
| Karaya | 20 | 20 | 20 | | | | | 20 | 20 | 20 | 20 | | | | |
| xanthane | | | | 20 | 30 | | | | | | | 20 | 20 | 20 | 20 |
| tragacanth | | | | | | 20 | 30 | | | | | | | | |
| glycerin (15% water) | | | | 60 | 50 | 60 | 50 | | | | | | | | |
| glycerin (30% water) | | | | | | | | 60 | | | | 60 | | | |
| glycerin (50% water) | | | | | | | | | 60 | | | | 60 | | |
| ethylene glycol (15% water) | 60 | | | | | | | | | | | | | | |
| ethylene glycol (30% water) | | | | | | | | | | 60 | | | | 60 | |
| ethylene glycol (50% water) | | | | | | | | | | | 60 | | | | 60 |
| 1,2-propylene glycol (15% water) | | 60 | | | | | | | | | | | | | |
| polyethylene glycol (MW 300; 15% water) | | | 60 | | | | | | | | | | | | |
| citric acid | 10 | 10 | 10 | 10 | 10 | 10 | 10 | 10 | 10 | 10 | 10 | 10 | 10 | 10 | 10 |
| triethanolamine | 10 | 10 | 10 | 10 | 10 | 10 | 10 | 10 | 10 | 10 | 10 | 10 | 10 | 10 | 10 |

While only a limited number of specific embodiments of the foregoing invention have been described, it is, nonetheless to be broadly construed and not to be limited except by the character of the claims appended hereto.

What we claim is:

1. A visco-elastic gel comprising as components 10 to 50% of a high molecular weight gum karaya, 90 to 20% of at least one polyol taken from the class consisting of ethylene glycol, propylene glycol, glycerine, and homologous $C_4$ alcohols, 0 to 30% of at least one non volatile acid soluble in said polyol, 0 to 30% of at least one non volatile base soluble in said polyol, all percentages being by weight and based on total weight of said gel, said polyol having a water content of 5 to 50% by weight based on said polyol, said components being physiologically acceptable, said gel having a pH of about 4 to 5.

2. A visco-elastic gel comprising as components 10 to 50% of a high molecular weight gum karaya, 90 to 20% of at least one polyol taken from the class consisting of ethylene glycol, propylene glycol, glycerine, and homologous $C_4$ alcohols, 5 to 30% of at least one non volatile acid soluble in said polyol, 5 to 30% of at least one non volatile base soluble in said polyol, all percentages being by weight and based on total weight of said gel, said polyol having a water content of 5 to 50% by weight based on said polyol, said components being physiologically acceptable.

3. An electrode comprising a contact and a visco-elastic gel for electrical connection with the skin, said gel comprising as components 10 to 50% of a high molecular weight gum karaya, 90 to 20% of at least one polyol taken from the class consisting of ethylene glycol, propylene glycol, glycerine, and homologous $C_4$ alcohols, 0 to 30% of at least one non volatile acid soluble in said polyol, 0 to 30% of at least one non volatile base soluble in said polyol, all percentages being by weight and based on total weight of said gel, said polyol having a water content of 5 to 50% by weight based on said polyol, said components being physiologically acceptable.

* * * * *